United States Patent [19]

Chaumette et al.

[11] Patent Number: 5,756,419

[45] Date of Patent: May 26, 1998

[54] PROCESS FOR THE CONVERSION OF SYNTHESIS GAS IN THE PRESENCE OF A CATALYST COMPRISING COBALT AND ADDITIONAL ELEMENTS

[75] Inventors: Patrick Chaumette, Bougival; Blaise Didillon, Rueil Malmaison, both of France

[73] Assignee: Institut Francais du Petrole, Rueil-Malmaison, Cedex, France

[21] Appl. No.: 725,210

[22] Filed: Sep. 24, 1996

[30] Foreign Application Priority Data

Sep. 25, 1995 [FR] France .................. 95 11296

[51] Int. Cl.$^6$ .................. B01J 23/00; C07C 27/00; C07C 1/00
[52] U.S. Cl. .................. 502/313; 502/314; 502/322; 502/323; 502/327; 502/333; 502/334; 518/714; 518/715; 585/733
[58] Field of Search .................. 502/313, 314, 502/322, 323, 327, 333, 334; 518/714, 715; 585/733

[56] References Cited

U.S. PATENT DOCUMENTS

| | | | |
|---|---|---|---|
| 3,099,618 | 7/1963 | Gardner et al. | 208/112 |
| 5,086,027 | 2/1992 | Singhal et al. | 502/166 |
| 5,302,622 | 4/1994 | Chaumette et al. | 518/713 |

FOREIGN PATENT DOCUMENTS

| | | |
|---|---|---|
| 42 19 690 | 12/1992 | Germany . |
| 86/00296 | 1/1986 | WIPO . |
| 92/06784 | 4/1992 | WIPO . |

*Primary Examiner*—Glenn Caldarola
*Assistant Examiner*—In Suk Bullock
*Attorney, Agent, or Firm*—Millen, White, Zelano & Branigan, P.C.

[57] ABSTRACT

The invention concerns the preparation of a catalyst comprising a support containing at least one oxide of the element Si, Al, Ti, Zr, Sn, Zn, Mg or Ln (where Ln is a rare earth), cobalt, at least one element A selected from the group formed by ruthenium, platinum, palladium and uranium, and at least one element B selected from the group formed by molybdenum and tungsten, characterized in that it comprises at least the following successive steps:

(1) formation of a precursor comprising at least cobalt and at least a portion of the support;

(2) at least partial reduction of the precursor in the presence of at least one reducing compound; and (3) deposition of any part of compound present in the catalyst and not present in the precursor on the reduced precursor.

The invention also concerns the use of the catalyst in a process for the synthesis of $C_5^+$ hydrocarbons from synthesis gas.

10 Claims, No Drawings

PROCESS FOR THE CONVERSION OF SYNTHESIS GAS IN THE PRESENCE OF A CATALYST COMPRISING COBALT AND ADDITIONAL ELEMENTS

The present invention concerns a catalytic formulation, its preparation and its use in a process for the synthesis of hydrocarbons from a $CO$—$(CO_2)$—$H_2$ mixture, i.e., a $CO$—$H_2$ mixture which may contain $CO_2$, known as synthesis gas, more particularly its use to convert synthesis gas to a mixture of linear saturated hydrocarbons essentially constituted by $C_5^+$ hydrocarbons (i.e., containing at least 5 carbon atoms per molecule), or more precisely to a mixture of essentially linear saturated hydrocarbons containing at least 80% by weight of $C_5^+$ hydrocarbons with respect to the totality of the hydrocarbons formed.

The person skilled in the art is aware that synthesis gas can be converted to hydrocarbons in the presence of catalysts containing transition metals. This conversion is carried out at high temperature and under pressure and is known in the literature as the Fischer-Tropsch synthesis. Thus metals from group VIII of the periodic classification of the elements, such as iron, ruthenium, cobalt and nickel, catalyse the transformation of $CO$—$(CO_2)$—$H_2$ mixtures to liquid and/or gaseous hydrocarbons.

The products prepared by the Fischer-Tropsch synthesis in the presence of catalysts containing group VIII metals have a very wide distribution of molecular weights. Thus only a small proportion of the products obtained from atmospheric distillation such as that a person skilled in the art would carry out on a crude fall within the range of middle distillates constituted by kerosine and gas oil fractions, the kerosine fraction(s) being constituted by a mixture of hydrocarbons with boiling points in the range 140° C. to 300° C., and the gas oil fraction(s) being constituted by a mixture of hydrocarbons with boiling points in the range 180° C. to 370° C.

Major efforts have been made since 1973 to improve the yield of middle distillates from processes based on the conversion of synthesis gas. The catalyst described in U.S. Pat. No. 5,302,622, comprising cobalt, copper and ruthenium and prepared by gelation, produces a mixture of essentially linear saturated hydrocarbons containing at least 80% by weight of $C_5^+$ hydrocarbons with respect to the totality of the hydrocarbons formed.

The catalyst described in French patent FR-A-2 677 992 contains cobalt, at least one additional element M (for example in the form of the metal or in the form of the oxide) selected from the group formed by molybdenum and tungsten and at least one additional element N (for example in the form of the metal or in the form of an oxide) selected from the group constituted by elements from groups Ia, IIa, Ib (such as sodium, potassium, magnesium, calcium, copper or silver), ruthenium, palladium, uranium, praseodymium and neodymium, preferably from the group formed by sodium, potassium, ruthenium, copper and uranium, the totality of the elements being dispersed on a support which is preferably constituted by at least one oxide of at least one element selected from the group formed by the following elements: Si, Al, Ti, Zr, Sn, Zn, Mg, Ln (where Ln is a rare earth).

After calcining, the concentrations of the elements in the catalyst, expressed as the weight of the element with respect to the weight of support, are normally as follows:

1% to 60%, preferably 5% to 40% by weight, of cobalt;
0.1% to 60%, preferably 1% to 30%, by weight of element M;
0.01% to 15%, preferably 0.05% to 5%, by weight of element N.

The cobalt and the additional elements can be introduced using any method which is known to the person skilled in the art such as ion exchange, dry impregnation, co-precipitation, gelation, mechanical mixing or grafting of organometallic complexes. Impregnation or gelation techniques are preferably used.

After reduction in hydrogen, the catalyst of FR-A-2 677 992 can convert synthesis gas to a mixture of essentially linear saturated hydrocarbons containing at least 80% by weight of $C_5^+$ hydrocarbons with respect to the totality of hydrocarbons formed. The use of impregnation or gelation techniques for cobalt and molybdenum and/or tungsten and at least one additional element N and optionally at least one element selected from the group formed by the support elements can produce a catalyst for converting synthesis gas to hydrocarbons which is stable, active and selective for $C_5^+$ hydrocarbons.

The present invention describes the preparation of a catalyst with stable performances which, after reduction in hydrogen, converts synthesis gas to a mixture of essentially linear saturated hydrocarbons containing at least 80% by weight of $C_5^+$ hydrocarbons with respect to the totality of the hydrocarbons formed. One of the particular advantages of the catalyst when used in the Fischer-Tropsch synthesis process is that a smaller amount of methane (a secondary, undesirable, product of the synthesis reaction) is produced than when using prior art catalysts, in particular when compared with the catalyst described in French patent FR-A-2 677 992.

The present invention concerns a process for the preparation of a catalyst comprising a support selected from the group formed by at least one oxide of an element selected from the group formed by the following elements: Si, Al, Ti, Zr, Sn, Zn, Mg or Ln (where Ln is a rare earth, i.e., an element with an atomic number in the range 57 to 71 inclusive), preferably selected from the group formed by silica, alumina, zirconia and titanium oxide, and, expressed as the % by weight of the element with respect to the weight of the support in the catalyst, 1% to 60%, preferably 2% to 50%, of cobalt, 0.01% to 20%, preferably 0.05% to 10%, of at least one additional element A selected from the group formed by ruthenium, platinum, palladium and uranium, and 0.01% to 20%, preferably 0.02% to 15%, of at least one additional element B selected from the group formed by molybdenum and tungsten, the process being characterized in that preparation of the catalyst comprises at least the following successive steps:

(1) formation of a precursor comprising at least cobalt and at least a portion, preferably the totality, of the support;
(2) at least partial reduction of the precursor in the presence of at least one reducing compound; and
(3) deposition of any part of compound present in the catalyst and not present in the precursor on the reduced precursor.

The invention also concerns the catalyst which can be obtained by the process of the invention, also a process for the synthesis of essentially linear saturated hydrocarbons containing at least 80% by weight of $C_5^+$ hydrocarbons with respect to the totality of the hydrocarbons formed, from a feed containing carbon monoxide CO, hydrogen and possibly carbon dioxide $CO_2$, the feed being known as synthesis gas.

Preferably, the B/Co molar ratio is normally less than 1, and more preferably it is normally in the range 0.01 to 0.9.

In a preferred implementation of the process of the invention, the precursor further comprises a portion of the element A present in the catalyst, the other portion of element A present in the catalyst being deposited on the reduced precursor in step (3).

In a further preferred implementation of the process of the invention, which may or may not be independent of the preceding implementations, the precursor also comprises the totality of element A present in the catalyst. In this case, at least a portion of element B, preferably the totality of element B, is deposited on the reduced precursor in step (3).

In a further preferred implementation of the process of the invention, which may or may not be independent of the preceding implementations, the precursor also comprises a portion of element B present in the catalyst, the other portion of element B present in the catalyst being deposited on the reduced precursor in step (3).

In a further preferred implementation of the process of the invention, which may or may not be independent of the preceding implementations, the precursor comprises both a portion of element A present in the catalyst and a portion of element B present in the catalyst, the other portion of elements A and B being deposited on the reduced precursor in step (3).

In a further preferred implementation of the process of the invention, which may or may not be independent of the preceding implementations, the precursor also comprises the totality of element B present in the catalyst. In this case, at least a portion of element A, preferably the totality of element A, is deposited on the reduced precursor in step (3).

The cobalt and additional elements A and B which are optionally present in the precursor can be introduced, in step (1), using any method which is known to the person skilled in the art, such as ion exchange, dry impregnation, co-precipitation, gelation, mechanical mixing or grafting of organometallic complexes.

Step (1) may be used to incorporate at least a portion of element A and/or a portion of element B into precursor of the catalyst used in accordance with the invention, but in no case can step (1) be used to incorporate both the totality of element A present in the catalyst and the totality of element B present in the catalyst.

Of these methods, impregnation or gelation are preferred for the preparation of the precursor in step (1), since these methods allow intimate contact between cobalt and any additional elements A or B.

The use of impregnation or gelation techniques for cobalt, optionally element A, optionally element B and optionally at least one element selected from the group formed by the elements of the support can generally produce a precursor for a catalyst for converting synthesis gas to hydrocarbons which is both stable, active and selective towards $C_5^+$ hydrocarbons and only slightly selective towards methane.

A preferred method for the preparation of the precursor of the catalyst used in accordance with the invention consists of impregnating at least a portion, preferably the totality, of the support using at least one aqueous solution (or in at least one appropriate solvent) containing cobalt, optionally all or a portion of additional elements A or B and optionally at least one element selected from the group formed by the support elements, for example in the form of a halide, nitrate, acetate, oxalate, sulphate, a complex formed with oxalic acid and oxalates, a complex formed with citric acid and citrates, a complex formed with tartaric acid and tartrates, a complex formed with another polyacid or an acid alcohol and their salts, a complex formed with acetyl acetonates, and any other inorganic or organometallic derivative containing cobalt and optionally all or a portion of additional element(s) A or B, the other possible portion of additional elements A or B and the element selected from the group formed by the support elements being subsequently impregnated in step (3).

In order to incorporate the optional portion of element B (Mo or W), it is also possible to use at least one ammonium molybdate or at least one ammonium tungstate such as ammonium molybdate, tetrahydrated ammonium heptamolybdate or ammonium metatungstate.

After each impregnation of cobalt, optional additional elements A or B and the element selected from the group formed by the elements of the support on the selected support, the precursor obtained is then heat treated, i.e., dried, using any method which is known to the person skilled in the art, for example in a stream of nitrogen or air at a temperature in the range 80° C. to 200° C., then calcined, for example in a stream of air or nitrogen at a temperature which is, for example, in the range 200° C. to 800° C.

It is also possible to prepare the precursor of the catalyst of the invention using the method which is described in detail in U.S. Pat. No. 3,975,302 which consists of preparing an impregnating solution from a solid amorphous gel and an alkanolamine then impregnating the support with that solution.

A further method for the preparation of the precursor of the catalyst of the invention, which method is preferred for the present invention, consists of preparing a gel containing cobalt, any elements A or B and optionally at least one element selected from the group formed by the elements of the support. This gelation preparation is carried out using any technique which is known to the person skilled in the art. However, two gelation preparation methods are preferable and are described below, the first method concerning the presence of element B alone in the precursor.

The first preferred gelation method consists of preparing a gel containing cobalt and optional element B using the technique described in U.S. Pat. No. 3,846,341 by substituting the iron salt described in that patent by a cobalt salt. Thus the gel containing cobalt, optional element B and at least a portion, preferably the totality, of the support can be prepared as described below.

An aqueous solution I of a salt of element B, for example ammonium paramolybdate if B is Mo, with a concentration in the range 1 to 12.5 atom.g of molybdenum per liter, is introduced into a reactor and stirred at a temperature below 20° C. An aqueous solution II containing a cobalt salt, preferably cobalt nitrate, in a concentration of more than 1 atom.g per liter is added to solution I. A colloidal suspension is obtained. The suspension may be set by gentle heating with slow stirring (v<1000 rpm). Ageing at a temperature of more than 10° C. results in a homogeneous gel. If necessary, the gel can be dehydrated at a temperature in the range 40° C. to 150° C., preferably in the range 50° C. to 90° C. It is then dried, using any means which is known to the person skilled in the art, for example in a stream of nitrogen or air, at a temperature in the range 80° C. to 200° C., then calcined, for example in a stream of nitrogen or air at a temperature which is, for example, in the range 200° C. to 800° C. All or a portion of the support can be introduced at any stage of the preparation described above; it is preferably introduced into solution I or into solution II, preferably in finely divided form, i.e., with grains which preferably have a size of less than 250 μm (1 m=1 micron =1 micrometer= $1 \times 10^{-6}$ m).

The second of the preferred gelation methods is described below.

It consists of preparing a gel obtained by mixing a solution I containing an organometallic compound, preferably an alkoxide of the support precursor element, dissolved in an organic solvent, preferably an alcohol, and an aqueous solution II containing a cobalt salt, optionally at least one salt of element A, optionally at least one salt of element B and optionally at least one element selected from the group formed by the elements of the support, and also containing an inorganic acid which accelerates gelation, such as nitric, hydrochloric, sulphuric or phosphoric acid. The cobalt salts, and any elements A or B or any element selected from the group formed by the elements of the support, are for example halides, nitrates, acetates, oxalates, sulphates, complexes formed with a polyacid or an acid alcohol and their salts or complexes formed with acetylacetonates, or any other inorganic derivative which is soluble in an aqueous solution. The mixture of solutions I and II, stirred in the presence of the acid, produces a gel which is formed in less than 10 minutes and at a temperature in the range 20° C. to 80° C. The gel formed is separated from the residual solvents using any means which is known to the person skilled in the art, for example by centrifuging or filtering then drying, for example in a stream of nitrogen or air at a temperature in the range 80° C. to 200° C., and finally calcined, for example in a stream of air or nitrogen at a temperature in the range 200° C. to 800° C.

Reduction step (2) of the precursor formed in step (1) is generally as described below.

The catalyst precursor is first pre-reduced by at least one reducing compound, for example selected from the group formed by hydrogen, carbon monoxide and formic acid, and optionally brought into contact with an inert gas (for example nitrogen) in a reducing compound/(reducing compound+inert gas) molar ratio in the range 0.001: to 1:1.

Reduction is carried out in the gaseous phase between 150° C. and 600° C., preferably between 200° C. and 500° C., between 0.1 MPa and 10 MPa and at an hourly space velocity in the range 100 to 40000 volumes of mixture per volume of catalyst per hour. Pre-reduction can also be effected in the liquid phase, the catalyst being suspended in an inert solvent, for example a paraffinic cut.

Step (3) for depositing on the precursor any part of compound present in the catalyst and not present in the precursor is carried out using any technique which is known to the person skilled in the art. The term "compound" generally means an element selected from the group formed by the elements of the support or element A or element B, with the exception of cobalt. A preferred method consists, for example, of impregnating the reduced precursor using at least one aqueous solution (or in at least one appropriate solvent) which may contain any element selected from the group formed by the elements of the support and all or a portion of the additional element(s) A or B, for example in the form of a halide, nitrate, acetate, oxalate, sulphate, a complex formed with oxalic acid and oxalates, a complex formed with citric acid and citrates, a complex formed with tartaric acid and tartrates, a complex formed with another polyacid or acid alcohol and salts thereof, a complex formed with acetyl acetonates, and any other inorganic or organometallic derivative containing all or a portion of the additional element(s) A or B, the other optional portion of the additional element(s) A or B having already been impregnated in step (1).

The optional portion of element B (Mo or W) can be incorporated using at least one molybdate or at least one ammonium tungstate such as ammonium molybdate, tetrahydrated ammonium heptamolybdate or ammonium metatungstate.

After each impregnation of additional elements A or B, and the optional element selected from the group formed by the elements of the support, the catalyst obtained is dried using any means which is known to the person skilled in the art, for example in a stream of nitrogen or air at a temperature in the range 80° C. to 200° C. After drying, the catalyst can be calcined, for example in a stream of air or nitrogen at a temperature which is, for example, in the range 200° C. to 800° C.

It is also possible in step (3) to prepare the catalyst of the invention using the method described in detail in U.S. Pat. No. 3,975,302 which consists of preparing an impregnating solution from a solid amorphous gel and an alkanolamine, then impregnating the precursor formed in step (1) with the solution.

The catalyst can optionally be formed using any process which is known to the person skilled in the art, for example by extrusion, oil drop, bowl granulation or pelletization. After the forming step, the catalyst can optionally be dried under the operating conditions described above.

The catalysts of the invention differ from the prior art catalysts (FR-A-2 677 992 in particular) in that a larger proportion of elements A and/or B is deposited on the cobalt and not on the support. This can be seen, for example, by means of electron microscopic analysis and determination of local compositions by X ray emission.

The catalysts prepared using the operating procedures described above are particularly well suited for use in processes for the manufacture of a mixture of essentially linear saturated hydrocarbons containing at least 80% by weight of $C_5^+$ hydrocarbons with respect to the totality of the hydrocarbons formed, from synthesis gas.

The conditions for using these catalysts for the manufacture of hydrocarbons in accordance with the invention are normally as follows:

The catalyst, loaded into a reactor, is pre-reduced before use using at least one reducing compound, for example selected from the group formed by hydrogen, carbon monoxide and formic acid, optionally brought into contact with an inert gas (for example nitrogen) in a reducing compound/ (reducing compound+inert gas) molar ratio in the range 0.001:1 to 1:1.

Pre-reduction is carried out at 150° C. to 600° C., preferably at 200° C. to 500° C., at 0.1 to 10 MPa and at an hourly space velocity of 100 to 40000 volumes of mixture per volume of catalyst per hour. Pre-reduction can optionally be carried out in a liquid phase comprising at least one hydrocarbon containing at least 5, preferably at least 10, carbon atoms per molecule if the hydrocarbon synthesis reaction is carried out in a liquid phase comprising at least one hydrocarbon containing at least 5, preferably at least 10, carbon atoms per molecule.

Conversion of synthesis gas to hydrocarbons is then carried out at a total pressure which is normally in the range 0.1 MPa to 15 MPa, preferably in the range 1 MPa to 10 MPa, the temperature generally being in the range 150° C. to 350° C., preferably in the range 170° C. to 300° C.

The hourly space velocity is normally in the range 100 to 20000 volumes of synthesis gas per volume of catalyst per hour, preferably in the range 400 to 5000 volumes of synthesis gas per volume of catalyst per hour, and the $H_2$/CO ratio in the synthesis gas is normally in the range 1:2 to 5:1, preferably in the range 1.2:1 to 2.5:1.

The catalyst is generally used in the form of a calibrated fine powder (about 10–700 m) or as particles with an equivalent diameter of about 2 to 10 mm, respectively in the presence of a liquid phase (under the operating conditions) and a gaseous phase, or a gaseous phase. The liquid phase may be constituted by at least one hydrocarbon containing at least 5, preferably at least 10, carbon atoms per molecule.

The catalysts of the invention are particularly active and stable for the synthesis of hydrocarbons from synthesis gas. They produce very little methane, which is an undesirable secondary product. Finally, the catalysts can produce essentially paraffinic hydrocarbons, the fraction with the highest boiling points being converted with a high yield to middle distillates (gas oil and kerosine cuts) by a hydroconversion process such as hydrocracking and/or catalytic hydroisomerisation.

The following examples illustrate the invention.

EXAMPLE 1

(In Accordance with the Invention): Catalyst E

A solution 1 containing 130 g of ethyl orthosilicate (TEOS) dissolved in 50 ml of ethanol and a solution 2 containing 46.3 g of hexahydrated cobalt nitrate, 0.21 g of ruthenium trichloride hexamine and 32 g of concentrated nitric acid dissolved in 80 $cm^3$ of water were mixed at ambient temperature with vigorous stirring.

After 15 minutes, hydrolysis of the TEOS produced a gel mass containing cobalt and ruthenium salts.

The gel was separated from the mother liquor, oven dried at 40°–120° C., then calcined in air at 600° C.

The catalyst precursor obtained was reduced at atmospheric pressure in a mixture of hydrogen and nitrogen containing 6% of hydrogen in nitrogen at between ambient temperature and 240° C., then in pure hydrogen at between 240° C. and 450° C.

A solution 3 was prepared which contained 5.2 g of hexacarbonyl molybdenum in solution in 100 ml of heptane in an inert atmosphere.

After cooling to ambient temperature in hydrogen, the precursor was added to solution 3 in an inert atmosphere, and the mixture was stirred until solution 3 had completely decolourized.

After evacuation of the hydrogen in an inert atmosphere and passivation in a mixture of 1% of oxygen in nitrogen, air was gradually allowed into contact with solution 3. The solid was filtered, oven dried at 120° C., then catalyst E obtained was loaded into a unit.

EXAMPLE 2

(In Accordance with the Invention): Catalyst F

A solution 1 containing 130 g of ethyl orthosilicate (TEOS) dissolved in 50 ml of ethanol and a solution 2 containing 46.3 g of hexahydrated cobalt nitrate, 24.15 g of tetrahydrated ammonium heptamolybdate and 32 g of concentrated nitric acid dissolved in 80 $cm^3$ of water were mixed at ambient temperature with vigorous stirring.

After 19 minutes, hydrolysis of the TEOS produced a gel mass containing cobalt and molybdenum salts.

The gel was separated from the mother liquor, oven dried at 40°–120° C., then calcined in air at 600° C.

The catalyst precursor obtained was reduced at atmospheric pressure in a mixture of hydrogen and nitrogen containing 6% of hydrogen in nitrogen at between ambient temperature and 240° C., then in pure hydrogen at between 240° C. and 450° C.

A solution 3 was prepared which contained 0.21 g of ruthenium trichloride hexamine in solution in 50 ml of heptane in an inert atmosphere.

After cooling to ambient temperature in hydrogen, the precursor was added to solution 3 in an inert atmosphere, and the mixture was stirred until solution 3 had completely decolourized.

After evacuation of the hydrogen in an inert atmosphere and passivation in a mixture of 1% of oxygen in nitrogen, air was gradually allowed into contact with solution 3. The solid was filtered, oven dried at 120° C., then catalyst F obtained was loaded into a unit.

EXAMPLE 3

(In Accordance with the Invention): Catalyst G

A solution 1 containing 130 g of ethyl orthosilicate (TEOS) dissolved in ethanol and a solution 2 containing 46.3 g of hexahydrated cobalt nitrate, 24.15 g of tetrahydrated ammonium heptamolybdate, 0.11 g of ruthenium trichloride hexamine and 32 g of concentrated nitric acid dissolved in 80 $cm^3$ of water were mixed at ambient temperature with vigorous stirring.

After 19 minutes, hydrolysis of the TEOS produced a gel mass containing cobalt, molybdenum and ruthenium salts.

The gel was separated from the mother liquor, oven dried at 40°–120° C., then calcined in air at 600° C.

The catalyst precursor obtained was reduced at atmospheric pressure in a mixture of hydrogen and nitrogen containing 6% of hydrogen in nitrogen at between ambient temperature and 240° C., then in pure hydrogen at between 240° C. and 450° C.

A solution 3 was prepared which contained 0.10 g of ruthenium trichloride hexamine in solution in 50 ml of heptane in an inert atmosphere.

After cooling to ambient temperature in hydrogen, the precursor was added to solution 3 in an inert atmosphere, and the mixture was stirred until solution 3 had completely decolourized.

After evacuation of the hydrogen in an inert atmosphere and passivation in a mixture of 1% of oxygen in nitrogen, air was gradually allowed into contact with solution 3. The solid was filtered, oven dried at 120° C., then catalyst G obtained was loaded into a unit.

EXAMPLE 4

(Comparative): Catalyst H

A solution 1 containing 130 g of ethyl orthosilicate (TEOS) dissolved in 50 ml of ethanol and a solution 2 containing 46.3 g of hexahydrated cobalt nitrate, 24.15 g of tetrahydrated ammonium heptamolybdate, 0.21 g of ruthenium trichloride hexamine and 32 g of concentrated nitric acid dissolved in 80 $cm^3$ of water were mixed at ambient temperature with vigorous stirring.

After 17 minutes, hydrolysis of the TEOS produced a gel mass containing cobalt, molybdenum and ruthenium salts.

The gel was separated from the mother liquor, oven dried at 40°–120° C., then calcined in air at 600° C. Catalyst H obtained was loaded into a unit.

Catalysts E to H prepared in Examples 1 to 4 thus finally contained 25% of cobalt, 5% of molybdenum and 0.18% of ruthenium, the % being expressed in weight % of each element with respect to the weight of silica.

EXAMPLE 5

Catalytic Tests

Catalysts E, F, G, H prepared as in Examples 1 to 4 were tested in a gas phase fixed bed in a unit which operated continuously using 20 $cm^3$ of catalyst.

Catalysts E to H were first reduced in situ at 240° C. by a mixture of hydrogen and nitrogen containing 6% of hydrogen in nitrogen, then by pure hydrogen at 450° C., at atmospheric pressure. The test conditions for the catalysts were as follows:

temperature: 240° C.
pressure: 2 MPa
hourly space velocity (vvh): 2000 h$^{-1}$
H$_2$:CO molar ratio: 2:1

TABLE 1

CONVERSION OF SYNTHESIS GAS TO HYDROCARBONS

| CATALYST | CO CONV. (% vol) | DISTRIBUTION OF HYDROCARBONS FORMED (wt %) | | |
|---|---|---|---|---|
| | | $C_1$ | $C_2$-$C_4$ | $C_5^+$ |
| E | 58 | 7.5 | 3.8 | 89.7 |
| F | 66 | 4.8 | 3.1 | 92.1 |
| G | 72 | 6.2 | 3.5 | 90.3 |
| H | 60 | 10.5 | 4.7 | 84.8 |

We claim:

1. A process for the preparation of a catalyst comprising a support selected from the group formed by at least one oxide of an element selected from the group formed by the following elements: Si, Al, Ti, Zr, Sn, Zn, Mg or Ln (where Ln is a rare earth) and, expressed as the weight % of the element with respect to the weight of the support, 1% to 60% of cobalt, 0.01% to 20% of at least one additional element A selected from the group formed by ruthenium, platinum, palladium and uranium, and 0.01% to 20% of at least one additional element B selected from the group formed by molybdenum and tungsten, the process being characterized in that preparation of the catalyst comprises at least the following successive steps:

(1) formation of a precursor from a portion of the compounds comprising the catalyst, said precursor comprising at least cobalt and at least a portion of the support;
   (2) at least partial reduction of the precursor in the presence of at least one reducing compound; and
   (3) deposition of compounds comprising the catalyst not present in the precursor, on the reduced precursor.

2. A process according to claim 1, in which the precursor further comprises a portion of the element A present in the catalyst, the other portion of element A present in the catalyst being deposited on the reduced precursor in step (3).

3. A process according to claim 1, in which the precursor further comprises the totality of element A present in the catalyst.

4. A process according to claim 1, in which the precursor further comprises a portion of element B present in the catalyst, the other portion of element B present in the catalyst being deposited on the reduced precursor in step (3).

5. A process according to claim 1, in which the precursor further comprises the totality of element B present in the catalyst.

6. A process according to claim 1, in which the support is selected from the group formed by silica, alumina, zirconia and titanium oxide.

7. A process according to claim 1, in which the precursor further comprises the totality of the support present in the catalyst.

8. A catalyst prepared using the preparation process defined in claim 1.

9. A process for the synthesis of essentially linear saturated hydrocarbons containing at least 80% by weight of $C_5^+$ hydrocarbons with respect to the totality of the hydrocarbons formed, from a synthesis gas CO—(CO$_2$)—H$_2$, in the presence of a catalyst according to claim 8, in which conversion of the synthesis gas to hydrocarbons is carried out at a total pressure in the range 0.1 to 15 MPa, the temperature is in the range 150° C. to 350° C., the hourly space velocity is in the range 100 to 20000 volumes of synthesis gas per volume of catalyst per hour, and the H$_2$/CO molar ratio in the synthesis gas is in the range 1:2 to 5:1.

10. A process according to claim 9, in which the catalyst is pre-reduced before use, said pre-reduction being carried out using at least one reducing compound, which is optionally brought into contact with an inert gas in a reducing compound/(reducing compound+inert gas) molar ratio in the range 0.001:1 to 1:1, pre-reduction being carried out between 150° C. and 600° C., preferably between 200° C. and 500° C., between 0.1 and 10 MPa and at an hourly space velocity of 100 to 40000 volumes of mixture per volume of catalyst per hour.

* * * * *